United States Patent
Wildemeersch

(10) Patent No.: US 6,588,429 B1
(45) Date of Patent: Jul. 8, 2003

(54) METHOD FOR RETAINING AND ACTUATING AN INTER-UTERINE DEVICE INSERTER AND INSERTER ENABLING SAID METHOD TO BE CARRIED OUT

(76) Inventor: Dirk Wildemeersch, Vossenhul 8, B-8301 Knokke-Heist (BE)

( * ) Notice: Subject to any disclaimer, the term of this patent is extended or adjusted under 35 U.S.C. 154(b) by 0 days.

(21) Appl. No.: 09/958,582
(22) PCT Filed: Apr. 13, 2000
(86) PCT No.: PCT/BE00/00035
§ 371 (c)(1), (2), (4) Date: Oct. 11, 2001
(87) PCT Pub. No.: WO00/62725
PCT Pub. Date: Oct. 26, 2000

(30) Foreign Application Priority Data

Apr. 16, 1999 (BE) .............................. 9900266

(51) Int. Cl.⁷ .................................. A61F 6/06
(52) U.S. Cl. ...................... 128/830; 128/840
(58) Field of Search ............... 128/830–841; 604/891

(56) References Cited

U.S. PATENT DOCUMENTS 3,840,005 A * 10/1974 Walker ...................... 128/839
3,954,103 A * 5/1976 Garcia-Roel et al. ........ 128/839
4,655,204 A * 4/1987 Basuyaux ................... 128/839
4,949,732 A 8/1990 Spoon et al.

FOREIGN PATENT DOCUMENTS

| EP | 0 160 633 | 11/1985 |
| EP | 0 191 747 | 8/1986 |
| EP | 0 584 628 | 3/1994 |
| FR | 2 620 935 | 3/1989 |

* cited by examiner

*Primary Examiner*—Michael A. Brown
(74) *Attorney, Agent, or Firm*—Collard & Roe, P.C.

(57) ABSTRACT

The subject-matter of the invention is a method of retaining and operating an inserter of an intrauterine contraceptive device, and an inserter permitting the application of this method.

To this end, the method which, in an inserter of an intrauterine contraceptive device comprising a sheath 4, a needle 1 housed in the sheath and firmly fixed to a thumb-piece 3, and an intrauterine contraceptive device 15, also housed in the sheath, pulled by the needle and provided with a pull thread 22, consists firstly in firmly fixing needle 1 in relation to sheath 4 and maintaining pull thread 22 in the tensioned state, then in releasing needle 1 and pull thread 22, and is characterised in that the release of needle 1 conjointly ensures the release of pull thread 22.

14 Claims, 2 Drawing Sheets

METHOD FOR RETAINING AND ACTUATING AN INTER-UTERINE DEVICE INSERTER AND INSERTER ENABLING SAID METHOD TO BE CARRIED OUT

CROSS REFERENCE TO RELATED APPLICATIONS

Applicant claims priority under 35 U.S.C. §119 of Belgium Application No. 9900266 filed Apr. 16, 1999. Applicant also claims priority under 35 U.S.C. §120 of PCT/BE00/00035 filed Apr. 13, 2000. The international application under PCT article 21(2) was not published in English.

SUMMARY OF THE INVENTION

The subject-matter of the present invention is a method of retaining and operating an inserter of an intrauterine contraceptive device.

Further subject-matter of the invention is an inserter of an intrauterine contraceptive device (hereinafter IUCD) for the application of this method.

STATE OF THE ART

Methods and devices for inserting IUCDs, and especially IUCDs the cooperation of which with an insertion needle is maintained by a pull thread are known, for example from patent EU 0 160 633, in FIGS. 12 and 13 of which such a device is illustrated. In it the pull thread is retained simply by folding it beyond the proximal edge of the inserter. Such an embodiment does not permit the formation of single-use inserters provided at the outset with an IUCD retained on the needle in a reliable manner and forming a sterile assembly ready for use.

To this end, it has already been proposed in EU 0 191 747 to provide a retaining element for the pull thread in the form of a slit, as well as a blocking device releasable from the sheath on the needle. However, the method of operating this inserter requires that the blocking of the thread and of the sheath are released separately, which firstly carries the risk that the cooperation of the IUCD and the needle might be broken in the course of manipulation and in the course of operating the inserter, before the insertion of the element retaining the IUCD in the wall of the uterus has been completed, and, secondly, makes it difficult to operate said device with one hand, and, furthermore, once the operation of the inserter has been completed this method carries the risk that the pull thread will be pinched between the needle and the sheath, resulting in the exertion of traction on the IUCD when the extractor is withdrawn.

The present invention aims to remedy these disadvantages and, above all, to simplify the procedure of operating the inserter in order to allow easy release of the pull thread without risk of breaking the cooperation between needle and IUCD.

Advantageous embodiments of the method according to the invention which, in particular, firstly ensure effective retention of the pull thread and secondly allow complete release of the latter, also after operation of the inserter, are the subject-matter of the invention.

The invention also aims to provide an inserter allowing the method according to the invention to be implemented. The specific features of the inserter permitting implementation of this method are the subject-matter of the invention.

BRIEF DESCRIPTION OF THE DRAWINGS

The invention will be better understood with reference to the description below in conjunction with the attached drawings which show, solely by way of example, various embodiments of the invention, in which:

FIG. 1 is a partial plan view of this embodiment of the invention, the needle being in a first position in the sheath, FIG. 2 is a partial, sectional side view corresponding to FIG. 1, FIGS. 3 to 5 are views similar to those in FIG. 2, corresponding to successive stages in the operation of the inserter, FIG. 6 is a cross-section, solely through the sheath, along line A—A in FIG. 3, FIG. 7 is a cross-section, solely through the thumb-piece, along line B—B in FIG. 3, FIGS. 8 to 10 show a partial sectional side view of a further embodiment of the invention in successive stages of operation.

DETAILED DESCRIPTION OF THE DRAWINGS

Figure 1:
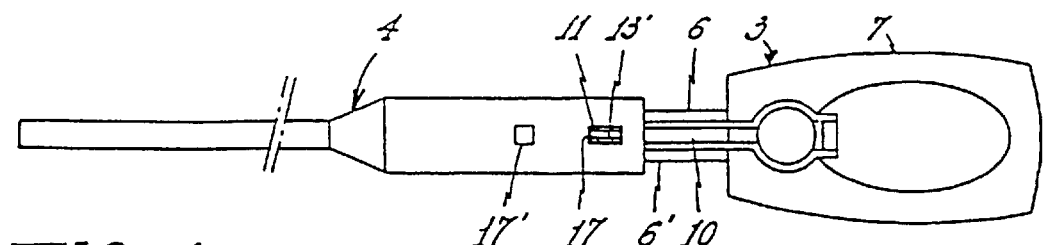
FIGS. 1 to 7 show various views of a preferred embodiment of the invention, and more particularly.

Referring to the preferred embodiment of the invention illustrated in FIGS. 1 to 7, the device according to the invention comprises a needle 1 firmly fixed at its proximal end 2 to a thumb-piece 3 and a sheath 4.

Thumb-piece 3 comprises a front portion 5 in which the proximal part 2 of needle 1 is fixed, connected by two arms 6, 6' to an operating plate 7 forming the thumb-piece itself. Said plate 7 is connected by an elastic loop 8 to a thruster 9 extending between arms 6, 6' in the form of a moving arm 10 provided with a projection 11. Front portion 5 also includes a projection 12 adapted to form a stop. A longitudinal groove 13 is formed in front portion 5 and, in prolongation of said groove 13, a groove 13' is formed in projection 11.

Sheath 4 includes a tubular portion 14 of small diameter adapted to receive needle 1 and an IUCD 15, and a widened base 16 adapted to receive and guide front portion 5 of the thumb-piece. In the widened base are formed two openings 17, 17', aligned to co-operate with projection 11 of the thumb-piece, a stop 18, a channel 19 forming a local widening of base 16 adapted to allow projection 12, which forms a stop on front portion 5, to pass. Also formed in base 16, in the prolongation of said channel 19, are a groove 20 adapted to allow projection 12 to pass and an elastic blade 21 adapted to rebound elastically beyond projection 12 when thumb-piece 3 is inserted into sheath 4. To facilitate reading of the drawing a pull thread 22 of IUCD 15 is represented by a dotted line. The cooperation of the IUCD and the needle is achieved through the intermediary of a fixing thread 23, fixed in known fashion to the distal end 24 of the needle by a knot and eye system 25.

During assembly the device is constructed as follows. An IUCD 15 is mounted on needle 1 by engaging knot and eye system 25 on distal end 24 of said needle, the cooperation of IUCD 15 and needle 1 being maintained by ensuring traction on pull thread 22. The pull thread is thus engaged in grooves 13, 13' of thumb-piece 3. Needle 1 is then inserted into sheath 4 until front portion 5 of thumb-piece 3 enters the widened base 16 of the sheath, where projection 12 clears channel 19 and engages in groove 20 until it passes beyond elastic blade 21. In this position projection 11 of the thumb-piece, in which pull thread 22 is engaged, engages in opening 17 of the thumb-piece up to the level of the bottom of groove 13', thus blocking pull thread 22 in the tensioned state. Needle 1 is thus fixed in relation to sheath 4 and immobilised in relation to it in a first position in which the distal end 24 of the needle does not project out of the sheath 4. The assembly can therefore be stored in a sterile manner, the inserter fitted with the IUCD being ready for use.

In use, when the inserter is operated, the latter has normally been inserted into the uterus until the end of the sheath 4, on tubular portion 14, has come into contact with the end of the uterus. Pressure exerted on thruster 9 in the direction of arrow 26 (see FIG. 3) causes projection 11 to be disengaged from opening 17 and in this way conjointly releases needle 1, which can be advanced in sheath 4, and pull thread 22, which is thus released from the tensioned state in which it had been held. It should be noted that in this position, during the joint release of needle 1 and pull thread 22, the cooperation of projection 12 and blade 19 prevents any retraction of the needle into the sheath which might cause disengagement of knot and eye system 25 from distal end 24 of needle 1.

Needle 1 is then advanced in sheath 4 while its distal end 24, pulling IUCD 15, projects from tubular portion 14 of the sheath. As this movement takes place the pressure on thruster 9 is relaxed and pull thread 22 is maintained in grooves 13, 13', precluding any blockage of said pull thread 22 between sheath 4 and thumb-piece 3.

Figure 2:
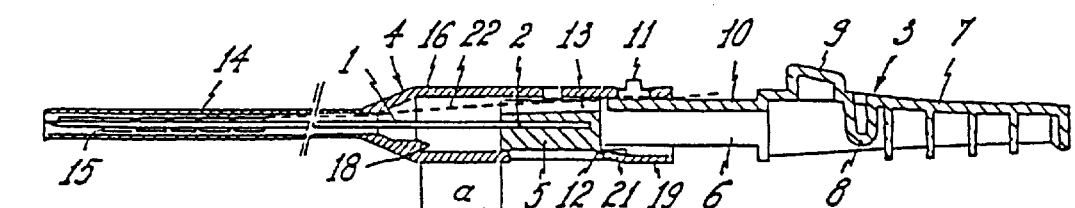
Figure 3:
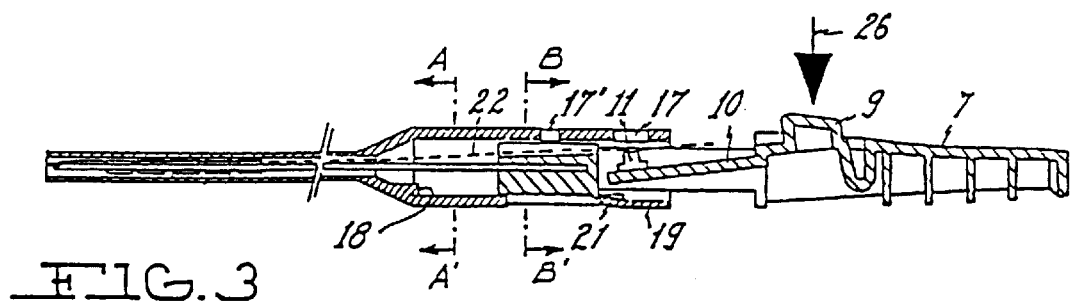
Figure 4:
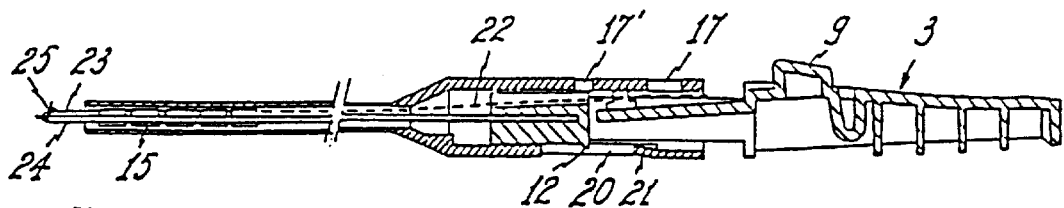
Figure 5:
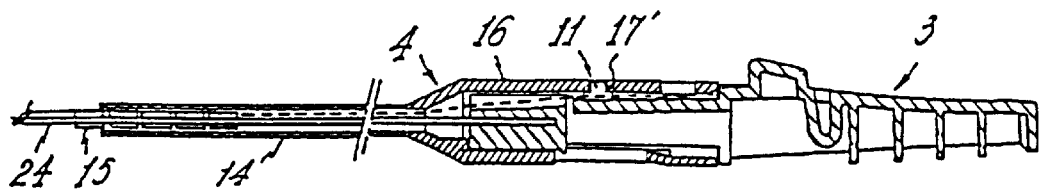
Figure 6:
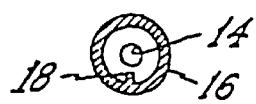
Figure 7:
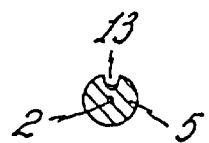

The maximum travel of needle 1 in sheath 4 corresponds to distance a in FIG. 2. Needle 1 which, in the first position, when it was released, was substantially in contact with blade 21 of sheath 4 through projection 12 of thumb-piece 3, ends its advance in sheath 4 when front portion 5 of the thumb-piece comes substantially into contact with stop 18 in the sheath. In this second position distal end 24 of the needle, pulling the IUCD, projects from the sheath by a predetermined distance which in practice is the distance suitable for fixing the IUCD in the uterus. On arriving at this second position, under the action of elastic loop 8 which permanently returns moving arm 10 to its initial position, the upper part of projection 11 engages in opening 17' while leaving free a sufficient part of groove 13' for pull thread 22 to move freely in it. Thus, needle 1 is blocked in sheath 4 in this second position while pull thread 22 remains entirely free. This blocking of needle 1 in sheath 4 now permits a retracting movement of the inserter (ensemble of sheath 4 and needle 1 firmly fixed to thumb-piece 3) by simple traction exerted on the thumb-piece, while IUCD 15, firmly fixed to knot and eye system 25 introduced into the tissue of the uterus and to pull thread 22, remains in place. The inserter can therefore be withdrawn without any risk of pinching pull thread 22 in said inserter, and therefore without risk of exerting traction on IUCD 15.

According to the preferred embodiment of the invention illustrated in FIGS. 1 to 7, projection 11, in which groove 13' is formed, has the form of a stepped shoulder. Opening 17 is sufficiently large to receive the whole of projection 11, while opening 17', which is shorter, receives only the upper part of the shoulder. This latter is offset from the base of groove 13' by a distance substantially equal to or greater than the thickness of pull thread 22.

It appears clearly from the above description that, owing to the simplicity of the operations to be carried out, the operation and the withdrawal of the inserter can be easily performed with one hand.

Figure 8:
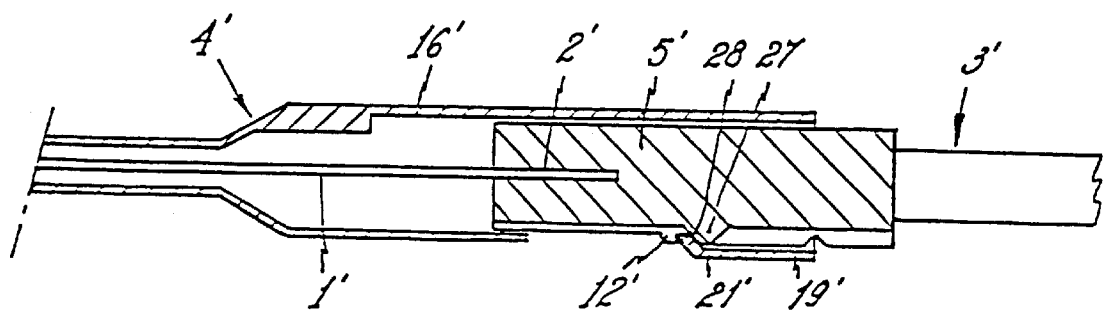
Figure 9:
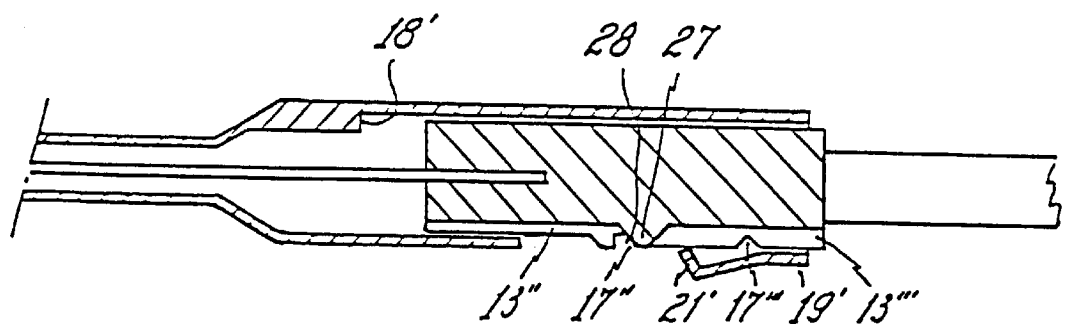
Figure 10:
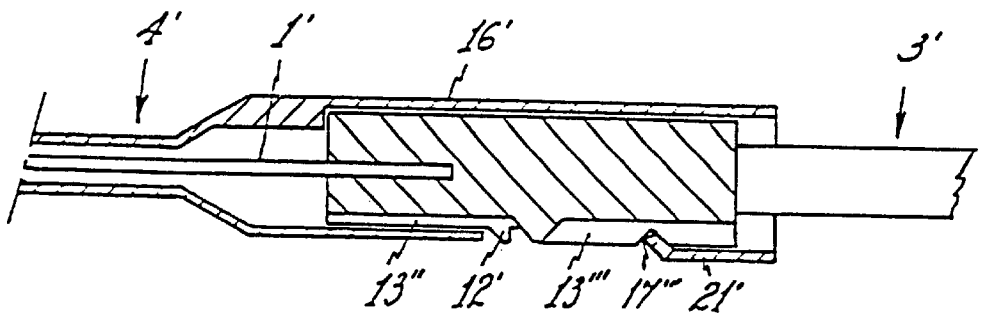

Another embodiment of the invention is illustrated by way of example in FIGS. 8 to 10.

In this other embodiment a front portion 5' of a thumb-piece 3' moves in a widened base 16' of a sheath 4'. Front portion 5' is prolonged on this side of a stop 12' adapted to co-operate with an elastic blade 21' of the sheath, and in this prolongation has two notches 17", 17''', also adapted to co-operate with elastic blade 21'. Front portion 5' also has two grooves 13", 13''' in prolongation of each other and separated by a solid boss 27. The pull thread (not shown) of the IUCD is adapted to be received in grooves 13", 13''' while passing over boss 27. The face 28 of boss 27 forming a wall of notch 17", through its cooperation with elastic blade 21', as illustrated in FIG. 8, forms at the same time a means of pinching the pull thread and, under the action of pressure exerted on thumb-piece 3', a means of releasing the needle and this thread, said face then acting as a ramp to dislodge the blade from notch 17".

At the end of the movement, when blade 21' comes into cooperation with the second notch 17''', the depth of groove 13''' is sufficient to ensure free movement of the pull thread, while the cooperation of blade 21' and notch 17''' permits simultaneous withdrawal of the inserter by simple traction exerted on the thumb-piece.

What is claimed is:

1. In a method of retaining and operating an inserter of an intrauterine contraceptive(hereinafter IUCD), in which the inserter comprises
    a sheath;
    a needle and an IUCD housed in said sheath, said needle being movable relative to said sheath, said needle having a proximal end and a distal end, said needle when housed in said sheath having a first position wherein said distal end does not emerge from said sheath, and a second position wherein said distal end projects a from said sheath when said IUCD is pulled, said proximal end of said needle being fixedly secured to a thumb-piece,
    said IUCD having a pull thread fixedly secured under tension to said distal end of said needle;
    said method including the steps of:
    fixedly securing said needle to said sheath to immobilise said needle in said first position wherein said distal end of said needle does not protrude from said sheath;
    maintaining said pull thread in a tensioned state to ensure a pulling action between said needle and said IUCD;
    releasing said pull thread in an operating phase; and,
    releasing said needle from said first position to place it in said second position during said operating phase whereby said distal end of said needle projects a predetermined distance from said sheath when said IUCD is pulled;
    the improvement comprising
    releasing said needle from said first position in said operating phase to conjointly release said pull thread.

2. The method according to claim 1, including the steps of, after release of said pull thread, maintaining said pull thread in a free condition during the subsequent operating phase of the inserter, and maintaining said needle in said second position after travel between said first and second positions.

3. The method according to claim 2, including the steps of blocking movement of said needle during operation of said inserter on a side being travelled from when said needle is in said first position on said side being travelled from and beyond when said needle is in said second position during operation of said inserter.

4. The method according to claim 1, including the steps of simultaneously maintaining tension on said pull thread while immobilizing said needle in said first position.

5. In an inserter for an IUCD comprising
a sheath;
a needle and an IUCD housed in said sheath, said needle being movable relative to said sheath, said needle having a proximal end and a distal end, and being fixedly secured to a thumb-piece; and,
    said IUCD having a pull thread, and being fixedly secured under tension to said distal end of said needle
the improvement wherein
    said sheath and said thumb-piece comprise:
        first cooperating blocking means, said blocking means being adapted to prevent movement of said needle when positioned in a sheath in a first position in which the distal end of said needle does not project from said sheath,
        means for maintaining said pull thread under tension; and
        releasing means, said releasing means being actuatable by said thumb-piece, enabling relative movement between said needle and said sheath in a direction of movement of said needle into said sheath, and wherein said releasing means is adapted to release said pull thread of said IUCD.

6. The inserter according to claim 5, wherein at least one groove which is substantially parallel to the direction of said needle is provided in at least one of said blocking means of said inserter to ensure said pull thread is maintained in a free state over an operating path of said inserter outside a first position of said first cooperating blocking means, and including second cooperating blocking means, said second blocking means being adapted to block relative movement between said needle and said sheath when said needle is in said second position, without restricting movement of said pull thread.

7. The inserter according to claim 6, wherein said second blocking means comprises a projection having a narrow upper portion and a second opening in said sheath, said first and said second openings of said sheath aligned longitudinally and having dimensions corresponding to said narrow upper portion, said second opening and said upper portion being elastically engagable to enable unrestricted movement of said pull thread in said groove.

8. The inserter according to claim 7, wherein said projection of said upper portion has a stepped shape in a plane parallel to the plane of said groove, said step being offset from the base of said groove by a distance substantially equal to or greater than a thickness of said pull thread.

9. The inserter according to claim 6, wherein said first blocking means comprises a blade and a first notch on said thumb-piece positioned immediately after said stop, said first notch having a face non-adjacent to said stop and shaped as an inclined ramp adapted to pinch said thread in cooperation with said blade and further to dislodge said blade under the effect of longitudinal pressure on said thumb-piece to enable movement of said thumb-piece and said needle.

10. The inserter according to claim 9, wherein said second cooperating blocking means comprises a blade and a second notch on said thumb-piece, said second notch being adapted to retain said blade when moved into engagement therewith to ensure retention of said needle relative to said sheath and without blocking said pull thread of said IUCD.

11. The inserter according to claim 5, wherein said inserter includes cooperating stop means positioned substantially corresponding to said first and second positions of said needle to thereby limit travel of said needle in said sheath between said first and said second positions.

12. The inserter according to claim 7, wherein said cooperating stop means, actuated when said needle occupies said first position in said sheath, comprise a blade formed on said sheath, said blade being elastically deformable whereby a stop on said thumb-piece can pass over said blade, and whereby said blade rebounds behind said stop preventing subsequent movement of said needle when said needle is in said first position.

13. The inserter according to claim 5, wherein said first blocking means comprises a first opening in said sheath and a projection on said thumb-piece with a groove permitting said pull thread to pass, said projection being elastically engageable in said first opening in said sheath to block said thumb-piece and movement of said needle with respect to said sheath, and to pinch said pull thread of said IUCD at said base at said groove.

14. The inserter according to claim 3, wherein said releasing means comprises a thruster connected to said projection, said thruster being elastically movable to disengage said projection from said first opening and to release relative movement between said needle and said sheath as well as being to release pinching of said pull thread.

* * * * *